US012343409B1

(12) United States Patent
Sturzbecher-Höhne et al.

(10) Patent No.: US 12,343,409 B1
(45) Date of Patent: Jul. 1, 2025

(54) RADIOPHARMACEUTICAL COMPOSITION AND METHODS

(71) Applicant: Ariceum Therapeutics GmbH, Berlin (DE)

(72) Inventors: Manuel Sturzbecher-Höhne, Berlin (DE); Dennis Mewis, Berlin (DE); Marion Huber, Berlin (DE)

(73) Assignee: Ariceum Therapeutics GmbH, Berlin (DE)

( * ) Notice: Subject to any disclaimer, the term of this patent is extended or adjusted under 35 U.S.C. 154(b) by 0 days.

(21) Appl. No.: 18/770,529

(22) Filed: Jul. 11, 2024

(30) Foreign Application Priority Data

Jun. 5, 2024 (EP) .................................... 24180333

(51) Int. Cl.
*A61K 51/04* (2006.01)
*A61K 47/22* (2006.01)

(52) U.S. Cl.
CPC .......... *A61K 51/0482* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 11,541,134 B1 | 1/2023 | Kim et al. |
| 11,819,556 B2 | 11/2023 | Kim et al. |
| 11,904,027 B2 | 2/2024 | de Palo et al. |
| 2008/0048942 A1 | 2/2008 | Ishida et al. |
| 2009/0129311 A1 | 5/2009 | Bruas |
| 2019/0243487 A1 | 8/2019 | Ryu et al. |
| 2019/0243489 A1 | 8/2019 | Xu et al. |
| 2024/0121249 A1 | 4/2024 | Rotstein et al. |

OTHER PUBLICATIONS

Handula (First preclinical evaluation of [225Ac]Ac-DOTA-JR11 and comparison with [177Lu]Lu-DOTA-JR11, alpha versus beta radionuclide therapy of NETs, Jun. 30, 2023, EJNMMI Radiopharmacy and Chemistry, 8(1):13) (Year: 2023).*
BASF (Technical Information—Kolliphor® HS 15, 2020, 03_111149e-04) (Year: 2020).*
ThermoFisher (Safety Data Sheet—PBS, PH 7.4, May 10, 2022) (Year: 2022).*
Handula, M. et al, "First preclinical evaluation of [225Ac] Ac-DOTA-JR11 and comparison with [177Lu] Lu-DOTA-JR11, alpha versus beta radionuclide therapy of NETs" EJNMMI Radiopharmacy and Chemistry, (2023), 8:13, pp. 1-16.
Hu, A. et al, "Chelating the Alpha Therapy Radionuclides 225Ac3+ and 213Bi3+ with 18-Membered Macrocyclic Ligands Macrodipa and Py-Macrodipa" Inorganic Chemistry 2022 61 (2), pp. 801-806.

* cited by examiner

*Primary Examiner* — Michael G. Hartley
*Assistant Examiner* — Kaila A Craig
(74) *Attorney, Agent, or Firm* — POLSINELLI PC

(57) ABSTRACT

The present invention relates to a liquid radiopharmaceutical composition comprising a radiopharmaceutical compound according to Formula I or a pharmaceutically acceptable salt thereof; and a buffer, wherein the buffer provides the radiopharmaceutical composition with a pH of about 7.0 to about 8.9. The present invention also relates to a pre-composition, starter composition, and kit, which can find use in preparing the liquid radiopharmaceutical composition, as well as to methods of preparing the liquid radiopharmaceutical composition, and medical uses of the liquid radiopharmaceutical composition.

11 Claims, 1 Drawing Sheet
Specification includes a Sequence Listing.

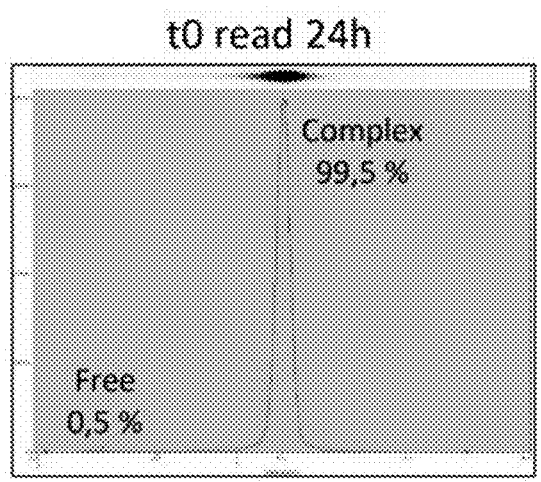
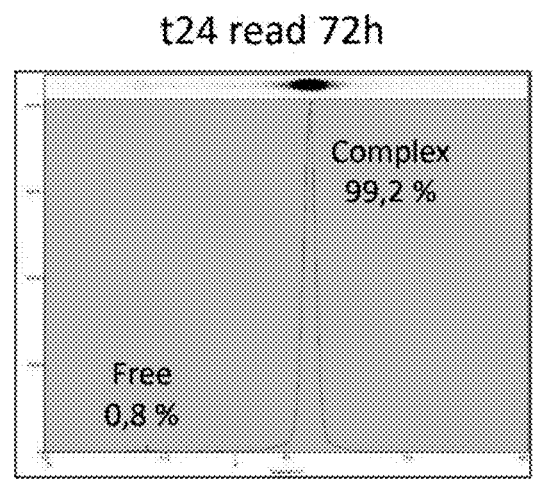
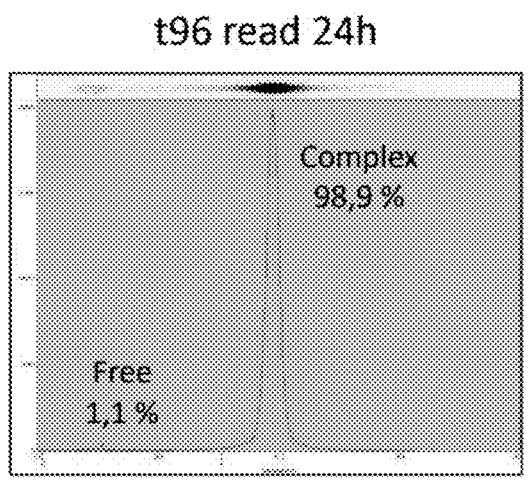
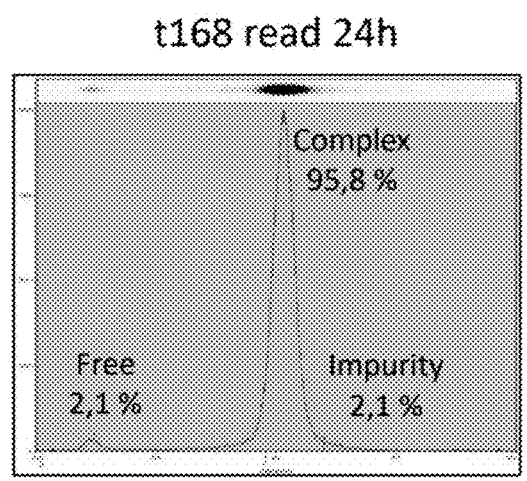

RADIOPHARMACEUTICAL COMPOSITION AND METHODS

CROSS REFERENCE TO RELATED APPLICATIONS

This application claims priority to European Patent Application No. 24180333.7 filed on Jun. 5, 2024, the entire content of which is incorporated herein by reference for its entirety.

SEQUENCE LISTING

This application contains a Sequence Listing that has been submitted in XML format via Patent Center and is hereby incorporated by reference in its entirety. The XML copy is named "P5246EP00_ST26_Sequence_Listing.xml", was created on Jul. 11, 2024 and is 4,266 bytes in size.

TECHNICAL FIELD

This invention relates to the field of radiopharmaceutical compositions. In particular, though not exclusively, the invention relates to improved techniques for preparing [$^{225}$Ac]Ac-DOTA-satoreotide and improved compositions relating thereto.

BACKGROUND

The use of radiopharmaceutical compounds in targeted radiopharmaceutical therapy has been receiving increased attention in recent years as a promising technique for targeted treatment of cancers. One particular compound used in targeted radionuclide therapy is the radiopharmaceutical compound according to Formula I:

(SEQ ID NO: 1), where the X at position 1 is para-chlorophenylalanine; the C at position 2 is D-cysteine; the X at position 3 is [(2,6-dioxo-hexahydro-pyrimidine-4-carbonyl)-amino]-phenylalanine; the X at position 4 is 4-aminophenylcarbamoyl (4-ureido-phenylalanine); the Y at position 8 is D-tyrosine; and the disulfide bridge is between positions 2 and 7.

Satoreotide belongs to a new generation of somatostatin analogues (SSAs). Unlike the first generation of SSAs, which were somatostatin receptor agonists, satoreotide is a somatostatin receptor antagonist, and it elicits its clinical properties by being able to bind with more binding sites than the agonist counterparts. In addition, as an antagonist, satoreotide is not internalized into the cell and thus remains available to bind to multiple receptor binding sites for longer periods of time. Furthermore, satoreotide shows a slower dissociation rate from the receptor than receptor agonists. When used in a radiopharmaceutical compound, satoreotide can target somatostatin-positive cancers, such as neuroendocrine tumors and/or small-cell lung cancer. When targeted in this way, the alpha particles emitted during decay of $^{225}$Ac damage cell compartments (e.g. DNA or cell membranes) within the targeted cells, leading to targeted cell death.

The alpha particles emitted by decay of radionuclides such as $^{225}$Ac have a greater ability to damage DNA than beta emitters and can therefore be more efficacious in bringing about cell death. Alpha particles are positively charged and have particle energy ranging from 5 to 9 MeV and a very short range of 40-100 μm. The range of the particle is thus considered to be equivalent to the thickness of 1-3 cell widths. The [$^{225}$Ac]Ac-DOTA-satoreotide radiopharmaceutical compound therefore holds immense promise for targeted alpha therapy (TAT) in cancer treatment (see, for example, Handula et al., *EJNMMI Radiopharmacy and*

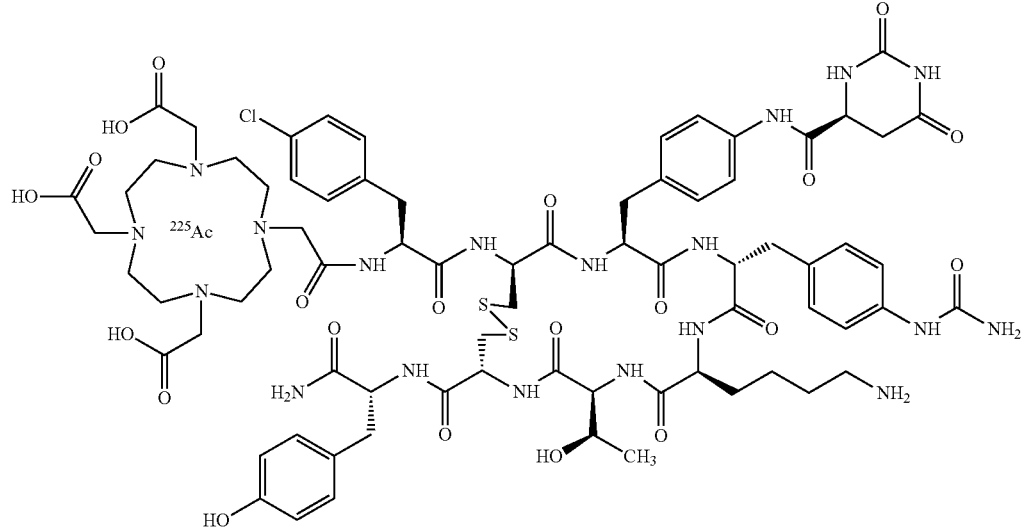

Formula I

The compound of Formula I is also known as [$^{225}$Ac]Ac-DOTA-satoreotide, or [$^{225}$Ac]Ac-tetraxetan-satoreotide, and is a complex comprising: the $^{225}$Ac radionuclide, which is an alpha emitter; DOTA (which can also be referred to as tetraxetan), which is a chelator of $^{225}$Ac; and satoreotide, which is a somatostatin antagonist. _Satoreotide is a cyclic peptide having the amino acid sequence of XCXXKTCY

*Chemistry*, (2023), 8:13, pages 1-16; and PCT/EP2023/084572; both of which are incorporated by reference in their entirety).

However, one drawback of utilising the more powerful alpha particles is that they can also degrade the components of the radiopharmaceutical compound. This degradative process is known as radiolysis. Radiolysis results in the radiochemical purity of the radiopharmaceutical composition decreasing as a function of time, meaning a shortened useful shelf-life of the radiopharmaceutical composition. For [$^{225}$Ac]Ac-DOTA-satoreotide, the shelf-life is measured in days (typically up to 5 days) starting from when the reaction to complex the $^{225}$Ac with the DOTA-satoreotide is complete (referred to as the 'end-of-production' time, or EOP time, also referred to herein as t=0h). The limited global supply of radiopharmacies that could commercially manufacture [$^{225}$Ac]Ac-DOTA-satoreotide can lead to long shipping times to reach distant healthcare facilities where the radiopharmaceutical is to be administered to a patient. Maintaining stability is therefore important to, for instance, maintain therapeutic efficacy and/or increase the time available to transport the radiopharmaceutical from a manufacturing facility to a healthcare facility. This could, for instance, allow for a greater radius of transportation from the manufacturing facility and/or allow for the use of more economic slower transport means.

Efforts have been made to optimise the production and storage of [$^{225}$Ac]Ac-DOTA-satoreotide. For instance, Handula et al is a recently published effort to optimise the method for radiolabelling of DOTA-satoreotide (referred to therein as DOTA-JR11) with [$^{225}$Ac]Ac(NO$_3$)$_3$. This method gives what is described as a high radiochemical yield of 95% and a high radiochemical purity of 94%. Stability in PBS and mouse serum was studied, and across the experiments performed the radiochemical purity was observed to be between 56.6% to 81.4% at time period of approximately 1 day (analyses were done at between 22 and 27 h).

The present invention aims to provide one or more improvements to [$^{225}$Ac]Ac-DOTA-satoreotide compositions and/or pre-compositions or methods related thereto, with respect to the prior art.

SUMMARY OF THE INVENTION

It has now been found that control of pH can provide unexpected advantages in [$^{225}$Ac]Ac-DOTA-satoreotide compositions and their preparation.

From a first aspect, the invention provides a liquid radiopharmaceutical composition comprising:
  a. a radiopharmaceutical compound according to Formula I

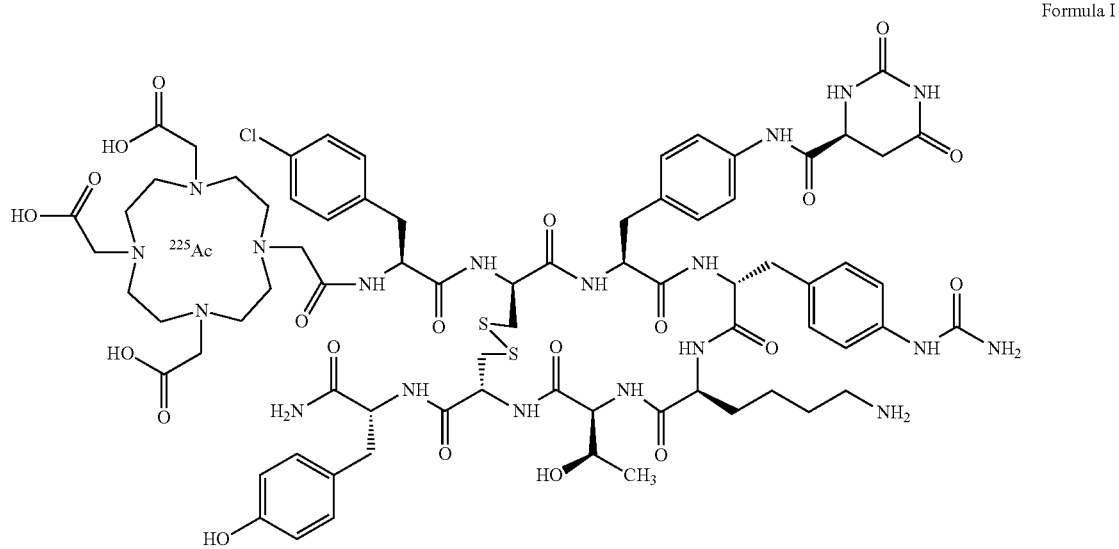

Formula I or a pharmaceutically acceptable salt thereof; and
  b. a buffer, wherein the buffer provides the radiopharmaceutical composition with a pH of about 7.0 to about 8.9.

From a second aspect, the invention provides a liquid radiopharmaceutical pre-composition comprising:
a. a precursor compound according to Formula II

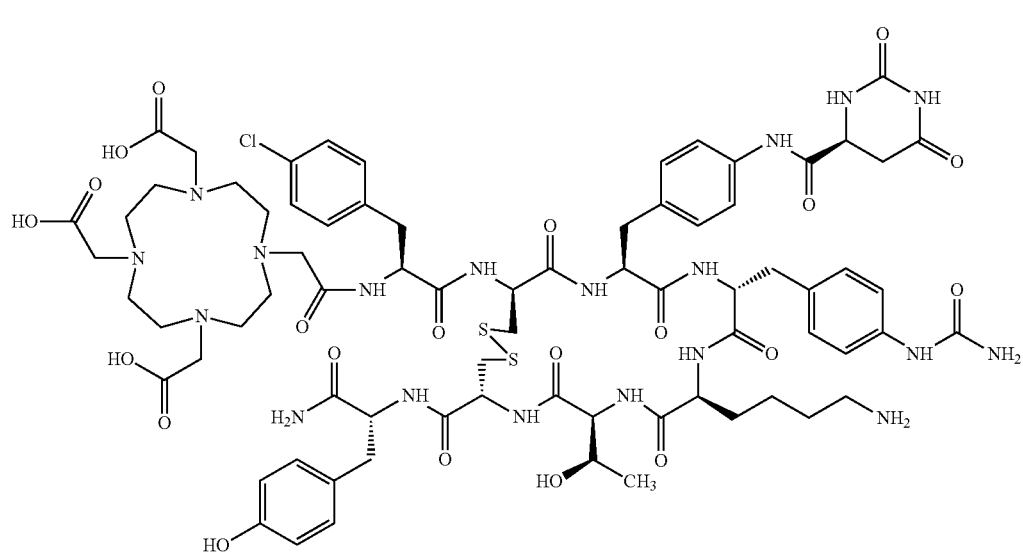

Formula II or a pharmaceutically acceptable salt thereof;
b. a buffer, wherein the buffer provides the liquid radiopharmaceutical pre-composition with a pH of about 7.0 to about 8.9; and
c. a [$^{225}$Ac]Ac$^{3+}$ salt.

From a third aspect, the invention provides a starter composition for the preparation of a liquid radiopharmaceutical pre-composition comprising:

d. a precursor compound according to Formula II

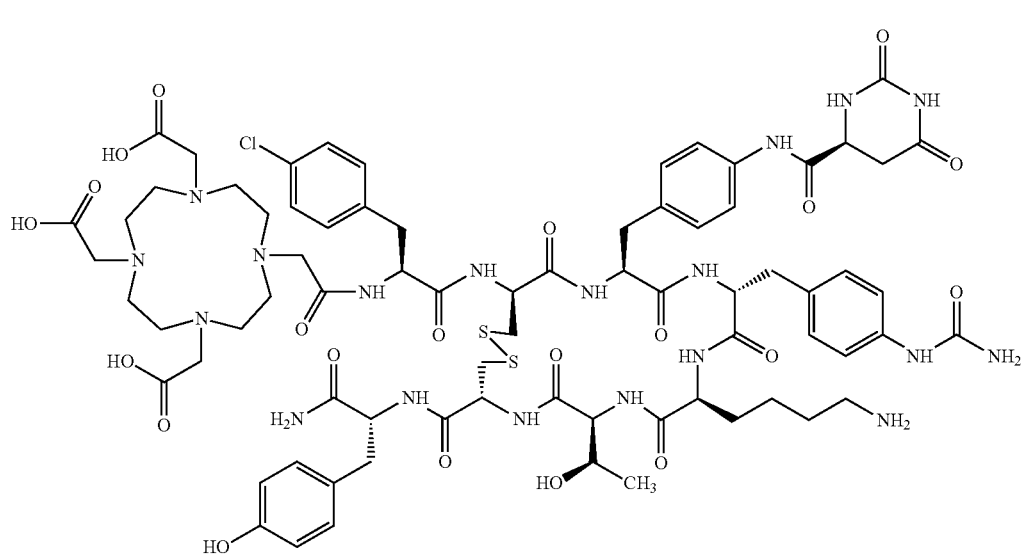

Formula II or a pharmaceutically acceptable salt thereof; and
e. a buffer, wherein the buffer is formulated to provide a pH of about 7.0 to about 8.9.

From a fourth aspect, the invention provides a method of preparing a liquid radiopharmaceutical composition, the method comprising:
  providing a liquid radiopharmaceutical pre-composition according to the second aspect;
  heating the liquid radiopharmaceutical pre-composition to generate a labelled composition;

cooling the labelled composition; and
diluting the labelled composition with a formulation solution; wherein the formulation solution comprises a formulation buffer that provides the liquid radiopharmaceutical composition with a pH of about 7.0 to about 8.9.

From a fifth aspect, the invention provides a kit comprising:
a. a precursor compound according to Formula II Formula II or a pharmaceutically acceptable salt thereof; and
b. a buffer, wherein the buffer is formulated to provide a pH of about 7.0 to about 8.9.

From a sixth aspect, the invention provides a liquid radiopharmaceutical composition according to the first aspect of the invention for use in treatment.

From a seventh aspect, the invention provides use of a liquid radiopharmaceutical composition according to the first aspect of the invention in the manufacture of a medicament for use in treatment.

From an eighth aspect, the invention provides a method of treatment of a patient in need thereof, the method comprising administering to a subject in need thereof a therapeutically effective amount of a liquid radiopharmaceutical composition according to the first aspect of the invention.

Throughout the description and claims of this specification, the words "comprise" and "contain" and variations of the words, for example "comprising" and "comprises", mean "including but not limited to", and do not exclude other components, integers or steps. The words "comprise" and "contain" and variations of the words, for example "comprising" and "comprises", as used herein, also disclose the embodiment, where appropriate, where no features other than the specifically mentioned features are present, excepting trace impurities, as denoted by the phrase "consist essentially of", and variations of this phrase, for example "consisting essentially of" and "consists essentially of", and also the embodiment where no features other than the specifically mentioned features are present as denoted by the phrase "consist of", and variations of this phrase, for example "consisting of" and "consists of", such that any instances of "comprise" may be replaced by "consist essentially of" or "consist of", and likewise for the variations of these phrases. For example, a disclosure of "comprising a feature" is also a disclosure of "consisting of a feature", such that "comprising a feature" may be limited, if desired, to "consisting of a feature". Moreover, the singular encompasses the plural unless the context otherwise requires: in particular, where the indefinite article is used, the specification is to be understood as contemplating plurality as well as singularity, unless the context requires otherwise. The word "about" when preceding any value is also a disclosure of that value without the word "about", e.g. a disclosure "about 5 g" is also to be considered a disclosure of "5 g".

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

DETAILED DESCRIPTION

Definitions

As used herein, the term "[$^{225}$Ac]Ac-DOTA-satoreotide" is synonymous with the compound of Formula I, and the term "DOTA-satoreotide" is synonymous with the compound of Formula II.

The term "somatostatin receptor (SSTR)" refers to receptors for the ligand "somatostatin", a small neuropeptide associated with neural signalling, particularly in the postsynaptic response to NMDA receptor co-stimulation/activation and also known as growth hormone-inhibiting hormone (GHIH). Somatostatin regulates the endocrine system and affects neurotransmission and cell proliferation via its receptors which are G protein coupled seven transmembrane receptors. Somatostatin has two active forms produced by the alternative cleavage of a single preproprotein: one consisting of 14 amino acids, the other consisting of 28 amino acids. Among vertebrates, there exist six different somatostatin genes that are designated SS1, SS2, SS3, SS4, SS5 and SS6. The six different genes, along with the five different somatostatin receptors, allow somatostatin to possess a large range of functions. Humans have only one somatostatin gene. Somatostatin receptors (SSTR1, 2A and B, 3, 4 and 5) have a wide expression pattern in both normal tissues and solid tumors. They are involved in the regulation of signalling cascades that suppress tumor cell proliferation, survival and angiogenesis. There are five known human somatostatin receptor subtypes: SST1 (SSTR1); SST2 (SSTR2); SST3 (SSTR3); SST4 (SSTR4); and SST5 (SSTR5).

Somatostatin receptors are expressed in pathological states, particularly in neuroendocrine tumors of the gastrointestinal tract. Most human tumors originating from the somatostatin target tissue have conserved their somatostatin receptors. It was first observed in growth hormone producing adenomas and TSH-producing adenomas; about one-half of endocrine inactive adenomas display somatostatin receptors. Ninety percent of the carcinoids and a majority of islet cell carcinomas, including their metastasis, usually have a high density of somatostatin receptors. However, only 10 percent of colorectal carcinomas and none of the exocrine pancreatic carcinomas contain somatostatin receptors. The somatostatin receptors in tumors can be identified using in vitro binding methods or using in vivo imaging techniques known in the art, the latter allowing the precise localization of the tumors and their metastasis in the patients. Somatostatin receptors have widespread but variable tissue expression in normal tissue. They are diversely expressed in multiple tumor types including a subset of breast, prostate, pancreatic, neuroendocrine, Merkel-cell carcinomas and hepatocellular carcinomas.

The "somatostatin receptor 2" (SSTR2) is overexpressed in a majority of neuroendocrine neoplasms, including inter alia small-cell lung carcinomas (SCLCs). SSTR2 is the best characterized member of the SSTR family and has multiple direct and indirect effects on cell cycling, angiogenesis, apoptosis and growth factor signaling. SSTR2s have been found in concentration on the surface of tumor cells, particularly those associated with the neuroendocrine system A synthetic version of the somatostatin hormone, octreotide, acting as an SSTR2 agonist, has been successfully used in combination with radio-peptide tracers to locate adrenal gland tumors through scintigraphic imaging. The use of SSTR2 and SSTR5 as biomarkers to track the progress of and treat neuroendocrine tumors comprising circulating tumor cells is also being investigated due to these cells' somatostatin receptor gene expressivity. There are several somatostatin analogues to target SSTRs that can be used as positron emission tomography (PET) radioligands to visualize neuroendocrine tumors. Ligands for SSTRs can be divided into agonists and antagonists.

The term "somatostatin receptor agonist" refers to analogues of the naturally occurring ligand somatostatin as described herein above. Examples of somatostatin receptor agonists are octreotide, octreotate, lanreotide or pasireotide.

The term "somatostatin receptor antagonist" refers to a molecule that binds to a somatostatin receptor (SSTR) and antagonizes the effects of the natural agonist somatostatin, for example diminishes or decreases a biological response induced by binding of said agonist upon binding to the receptor, i.e. the antagonist deactivates the biological function of the receptor upon binding rather than activating it upon binding, such as an agonist would do. Somatostatin receptor antagonists are not internalized into the cell upon binding to the receptor and thus, can bind to a larger number of receptors because they are independent of the receptor activation state.

The term "chelator" refers to a molecule or part of a molecule which is capable of complexing ions, such as $[^{225}Ac]Ac^{3+}$. Aspects of the invention relate to compounds comprising DOTA. DOTA is a chelator capable of chelating $^{225}Ac$. DOTA can also be referred to as tetraxetan. DOTA can also be referred to by the chemical name 2,2', 2'', 2'''-(1,4,7,10-tetraazacyclododecane-1,4,7,10-tetrayl)tetraacetic acid. DOTA can also be referred to by its chemical structure, which is set out in the formula below:

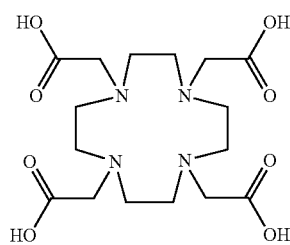 [SMILES: O=C(O)CN1CCN(CC(=O)O)CCN(CC(=O)O)CCN(CC(=O)O)CC1]

The "activity" of a given amount of radioactive material, or of a composition containing a radioactive material, is defined as the number of decays per unit of time. The SI unit of said activity is Becquerel (Bq) which amounts to one decay per second. The legacy unit of activity is denoted Ci. 1 MBq equals 27 µCi and 1 mCi equals 37 MBq, for example.

The term "specific activity" refers to the measured activity per gram of compound, measured in Bq/g.

The term "radiochemical yield (RCY)" refers to the amount of activity in the radiolabeled compound, after a process (such as at EOP), compared to the total initial activity before the process, and expressed as a percentage %.

The term "radiochemical purity (RCP)" refers to the proportion of the total radioactivity in the sample which is present as the radiolabeled compound expressed as a percentage %.

The term "neuroendocrine tumor (NET)" refers to a type of cancer. The term NET is an umbrella term for a group of relatively uncommon cancers originating in the neuroendocrine cells of numerous organs. The term "neuroendocrine" refers to the dual features of these cells which are a cross between nerve cells and hormone-producing endocrine cells, i.e. such cells produce neuropeptides and hormones. NETs are considered rare, however, since NETs are often slow-growing and generally associated with prolonged survival, there are many more people living with the disease. NETs appear mostly in the gastrointestinal tract, pancreas Langerhans islets, and the bronchopulmonary system beyond the hypophysis, thyroid, pancreas and adrenal glands. NETs frequently express multiple SSTRs with SSTR2 being expressed at the highest level. Small cell lung cancer (SCLC) is a high-grade poorly differentiated and metastatic neuroendocrine carcinoma of the lung. SCLC is associated with early metastasis and poor patient survival. Merkel cell carcinoma is a rare form of skin cancer.

Aspects of the invention relate to compositions and methods that make use of a particular pH range. The inventors have identified that use of a pH in the ranges disclosed herein can, for example, lead to an enhanced radiochemical yield and/or enhanced stability.

The viability of the pH ranges used herein was surprising. Many 3+ cationic metals form insoluble hydroxide precipitates at alkaline pH values, and therefore procedures requiring 3+ cationic metals are generally conducted at acidic pH. However, it has been found that $^{225}Ac^{3+}$, unusually, does not hydrolyse until about pH 9.0. Furthermore, it has been found that, surprisingly, conducting complexation at a pH between 7.0 and 8.9 can provide for an improved radiochemical yield and/or enhanced stability.

Liquid Radiopharmaceutical Composition

Aspects of the invention relate to a liquid radiopharmaceutical composition comprising: a. a radiopharmaceutical compound according to Formula I or a pharmaceutically acceptable salt thereof; and b. a buffer, wherein the buffer provides the radiopharmaceutical composition with a pH of about 7.0 to about 8.9.

Suitably, the liquid radiopharmaceutical composition may be a pharmaceutically acceptable composition. The liquid radiopharmaceutical composition may be formulated to be suitable for administration to a patient.

The buffer provides the radiopharmaceutical composition with a pH of about 7.0 to about 8.9. Optionally, the buffer may provide the radiopharmaceutical composition with a pH of at least about 7.1, 7.2, 7.3, 7.4, 7.5, 7.6, 7.7, 7.8 or 7.9. Suitably, the buffer may provide radiopharmaceutical composition with a pH of up to about 8.8, 8.7, 8.6, 8.5, 8.4, 8.3, 8.2 or 8.1. Advantageously, the buffer may provide the radiopharmaceutical composition with a pH of about 7.1 to about 8.9, about 7.2 to about 8.8, about 7.3 to about 8.7, about 7.4 to about 8.6, about 7.5 to about 8.5, about 7.6 to about 8.4, about 7.7 to about 8.3, about 7.8 to about 8.2, or about 7.9 to about 8.1. For example, the buffer may provide the radiopharmaceutical composition with a pH of about 8.0. Suitably, the buffer may be a pharmaceutically acceptable buffer. The skilled person is able to select a suitable buffer, using common techniques known in the art, that is suitable for maintaining such a pH. Optionally, the buffer may be is selected from: Tris, HEPES, TES, MOPS, imidazole buffer, CAPS, ACES, TAPS, or a combination thereof. In some embodiments, the buffer is Tris buffer.

Suitably, the radiopharmaceutical compound may be present at a concentration equivalent to about 0.1 MBq/mL to about 0.5 MBq/mL based on the total volume of the liquid radiopharmaceutical composition. Advantageously, the radiopharmaceutical compound may be present at a concentration equivalent to at least about 0.15 MBq/mL, 0.2 MBq/mL, or 0.25 MBq/mL based on the total volume of the liquid radiopharmaceutical composition. Optionally, the radiopharmaceutical compound is present at a concentration equivalent up to about 0.45 MBq/mL, 0.4 MBq/mL, or 0.35 MBq/mL based on the total volume of the liquid radiopharmaceutical composition. Advantageously, the radiopharmaceutical compound may be present at a concentration equivalent to about 0.15 MBq/mL to about 0.45 MBq/mL, about 0.2 MBq/mL to about 0.4 MBq/mL, about 0.25 MBq/mL to about 0.3 MBq/mL, or about 0.3 MBq/mL based on the total volume of the liquid radiopharmaceutical composition.

Suitably, the buffer may be present at a concentration of between about 1 mM to about 100 mM based on the total volume of the liquid radiopharmaceutical composition. Advantageously, the buffer may be present at a concentration of between about 2 mM to about 70 mM, about 3 mM to about 50 mM, about 4 mM to about 40 mM, about 5 mM to about 30 mM, about 6 mM to about 25 mM, about 7 mM to about 28 mM, about 8 mM to about 14 mM, about 9 mM to about 11 mM, or about 10 mM based on the total volume of the liquid radiopharmaceutical composition.

Advantageously, the liquid radiopharmaceutical composition may comprise a stabiliser. The stabiliser can optionally be selected from ascorbic acid, gentisic acid, glutathione, methionine, hydroquinone, polyoxyethylene (20) sorbitan monooleate, or structural analogues thereof, or pharmaceutically acceptable salts thereof, or combinations thereof. Optionally, the stabiliser may comprise ascorbic acid or a pharmaceutically acceptable salt thereof. Suitably, the pharmaceutically acceptable salt may be a sodium or potassium salt.

Optionally, the stabiliser, advantageously ascorbic acid or a pharmaceutically acceptable salt thereof, may be present at a concentration of greater than 350 mM based on the total volume of the liquid radiopharmaceutical composition. Optionally, the stabiliser, advantageously ascorbic acid or a pharmaceutically acceptable salt thereof, may be present at a concentration of about 350 mM to about 2000 mM based on the total volume of the liquid radiopharmaceutical composition. Optionally, the stabiliser, advantageously ascorbic acid or a pharmaceutically acceptable salt thereof may be present at a concentration of greater than about 375 mM, 400 mM, 425 mM, 450 mM, 475 mM, 500 mM, 550 mM or 600 mM based on the total volume of the liquid radiopharmaceutical composition. Optionally, the stabiliser, advantageously ascorbic acid or a pharmaceutically acceptable salt thereof, may be present at a concentration of up to 2000 mM, 1500 mM, 1000 mM, 950 mM, 900 mM, 850 mM, or 800 mM based on the total volume of the liquid radiopharmaceutical composition. Optionally, the stabiliser, advantageously ascorbic acid or a pharmaceutically acceptable salt thereof, may be present at a concentration of about 350 mM to about 2000 mM, about 375 mM to about 1500 mM, about 400 mM to about 1000 mM, about 425 mM to about 950 mM, about 475 mM to about 900 mM, about 500 mM to about 850 mM, about 550 mM to about 800 mM, or about 600 mM to about 750 mM based on the total volume of the liquid radiopharmaceutical composition.

Advantageously, the liquid radiopharmaceutical composition may retain a radiochemical purity of >91% after 168 hours at ambient temperature. Optionally, the liquid radiopharmaceutical composition may retain a radiochemical purity of >92%, >93%, >94%, >95%, or >95.5% after 168 hours at ambient temperature. Ambient temperature may be taken as 25° C. 168 hours represents 168 hours from end-of-production. Radiochemical purity may be measured by radio TLC, suitably according to a method set out in the examples.

The liquid radiopharmaceutical composition may optionally comprise diethylenetriamine-N,N,N',N,N-pentaacetic acid (DTPA). For example, the liquid radiopharmaceutical composition may comprise DTPA at a concentration from about 0.01 mg/mL to about 0.2 mg/mL, about 0.05 mg/mL to about 0.15 mg/mL, or about 0.07 mg/mL to about 0.12 mg/mL based on the total volume of the liquid radiopharmaceutical composition.

Conveniently, the total volume of the liquid radiopharmaceutical composition may be about 1 mL to about 50 mL, about 5 mL to about 40 mL, about 10 mL to about 30 mL, about 15 mL to about 25 mL, about 18 mL to about 22 mL, or about 20 mL.

Suitably, the liquid radiopharmaceutical composition may comprise a pharmaceutically acceptable aqueous diluent. Advantageously, the liquid radiopharmaceutical composition may comprise a pharmaceutically acceptable aqueous diluent that is suitable for injection into a patient. Suitable aqueous diluents may, for example, comprise isotonic, sterile, saline solutions. Optionally, the aqueous diluent may be saline solution or sterile water for injection (SWFI). For example, the aqueous diluent may be SWFI.

The liquid radiopharmaceutical composition may be sterile.

Optionally, the liquid radiopharmaceutical composition may comprise a pharmaceutically acceptable carrier and/or excipient. Suitably, the pharmaceutically acceptable carrier and/or excipient may comprise one or more of: an antioxidant, selected from ascorbic acid, glutathione, cysteine, methionine, citric acid and combinations thereof; a preservative, selected from ethanol, benzyl alcohol, phenol, m-cresol, p-chlor-m-cresol, methyl or propyl parabens, benzalkonium chloride, or combinations thereof; an amino acid, selected from arginine, glycine, ornithine, lysine, histidine, glutamic acid, aspartic acid, isoleucine, leucine, alanine, phenylalanine, tyrosine, tryptophan, methionine, serine, proline or combinations thereof; a saccharide, selected from monosaccharides, disaccharides and other carbohydrates or combinations thereof; a low molecular weight polypeptide; a protein, including gelatine or serum albumin; a chelating agent including EDTA; a sugar, including trehalose, sucrose, lactose, glucose, mannose, maltose, galactose, fructose, sorbose, raffinose, glucosamine, N-methylglucosamine, galactosamine, and neuraminic acid; and/or a non-ionic surfactant, including Tween, Brij Pluronics, Triton-X, or polyethylene glycol (PEG).

Suitably, the liquid radiopharmaceutical composition may be formulated for parenteral application and may comprise one or more parenteral diluents. Parenteral administration comprises intravenous, intramuscular, subcutaneous and intradermal administration routes. Examples of parenteral diluents include sodium chloride solution, Ringer's dextrose, dextrose and sodium chloride, lactated Ringer's, or fixed oils. Intravenous diluents include fluid and nutrient replenishers, electrolyte replenishers (such as those based on Ringer's dextrose), and the like.

The form of the liquid radiopharmaceutical composition may depend upon the condition to be treated, the severity of the illness, the age, weight, and gender of the patient, the desired duration of the treatment etc. The liquid radiopharmaceutical composition in the context of this invention may be in any suitable form (depending upon the desired method of administering it to a patient). For example, it may be provided in a unit dosage form, which will generally be provided in a sealed container and may be provided as part of a kit.

Optionally, the radiopharmaceutical compound is not present at a concentration equivalent to 0.3 MBq/mL or 0.9 MBq/mL based on the total volume of the liquid radiopharmaceutical composition. Optionally, the radiopharmaceutical compound is not present at a peptide content of 10 μg/mL based on the total volume of the liquid radiopharmaceutical composition. Optionally, the radiopharmaceutical compound is not present at a concentration equivalent to 0.3 MBq/mL or 0.9 MBq/mL and at a peptide content of 10 μg/mL based on the total volume of the liquid radiopharmaceutical composition.

Liquid Radiopharmaceutical Pre-Composition

Aspects of the invention relate to a liquid radiopharmaceutical pre-composition comprising: a. a precursor compound according to Formula II or a pharmaceutically acceptable salt thereof; b. a buffer, wherein the buffer provides the liquid radiopharmaceutical pre-composition with a pH of about 7.0 to about 8.9; and c. a $[^{225}Ac]Ac^{3+}$ salt.

The buffer provides the radiopharmaceutical pre-composition with a pH of about 7.0 to about 8.9. Optionally, the buffer may provide the radiopharmaceutical pre-composition with a pH of at least about 7.1, 7.2, 7.3, 7.4, 7.5, 7.6, 7.7, 7.8 or 7.9. Suitably, the buffer may provide the radiopharmaceutical pre-composition with a pH of up to about 8.8, 8.7, 8.6, 8.5, 8.4, 8.3, 8.2 or 8.1. Advantageously, the buffer may provide the radiopharmaceutical pre-composition with a pH of about 7.1 to about 8.9, about 7.2 to about 8.8, about 7.3 to about 8.7, about 7.4 to about 8.6, about 7.5 to about 8.5, about 7.6 to about 8.4, about 7.7 to about 8.3, about 7.8 to about 8.2, or about 7.9 to about 8.1. For example, the buffer may provide the radiopharmaceutical pre-composition with a pH of about 8.0. Suitably, the buffer may be a pharmaceutically acceptable buffer. The skilled person is able to select a suitable buffer, using common techniques known in the art, that is suitable for maintaining such a pH. Optionally, the buffer may be selected from: Tris, HEPES, TES, MOPS, imidazole buffer, CAPS, ACES, TAPS or a combination thereof. In some embodiments, the buffer is Tris buffer.

The $[^{225}Ac]Ac^{3+}$ salt may suitably be present at a concentration equivalent to about 0.1 MBq/mL to about 20 MBq/mL based on the total volume of the liquid radiopharmaceutical pre-composition. Optionally, the $[^{225}Ac]Ac^{3+}$ salt may be present at a concentration equivalent to at least about 0.2, 0.3, 0.4 or 0.5 MBq/mL based on the total volume of the liquid radiopharmaceutical pre-composition. Optionally, the $[^{225}Ac]Ac^{3+}$ salt may be present at a concentration equivalent to up to about 18, 15, 13, or 11 MBq/mL based on the total volume of the liquid radiopharmaceutical pre-composition. Advantageously, the $[^{225}Ac]Ac^{3+}$ salt may be present at a concentration equivalent to about 0.2 MBq/mL to about 18 MBq/mL, about 0.3 MBq/mL to about 15 MBq/mL, about 0.4 MBq/mL to about 14 MBq/mL, or about 0.5 MBq/mL to about 11 MBq/mL, based on the total volume of the liquid radiopharmaceutical pre-composition The $^{225}Ac^{3+}$ salt can comprise any suitable salt. Optionally, the $^{225}Ac^{3+}$ salt may be a halide or nitrate. For example, the $^{225}Ac^{3+}$ salt is $^{225}AcCl_3$ or $^{225}Ac(NO_3)_3$. In some embodiments, the $^{225}Ac^{3+}$ salt is $^{225}AcCl_3$.

The precursor compound may suitably be present at a concentration of about 0.01 mg/mL to about 10 mg/mL based on the total volume of the liquid radiopharmaceutical pre-composition. Optionally, the precursor compound may be present at a concentration of at least about 0.05, 0.1, or 0.2 mg/mL based on the total volume of the liquid radiopharmaceutical pre-composition. Optionally, the precursor compound may be present at a concentration of up to about 5, 2, or 1 mg/mL based on the total volume of the liquid radiopharmaceutical pre-composition. Advantageously, the precursor compound may be present at a concentration of about 0.05 mg/mL to about 5 mg/mL, about 0.1 mg/mL to about 2 mg/mL, or about 0.2 mg/mL to about 1 mg/mL, based on the total volume of the liquid radiopharmaceutical pre-composition.

Suitably, the buffer may be present at a concentration of about 0.01 M to about 1 M based on the total volume of the liquid radiopharmaceutical pre-composition. Optionally, the buffer may be present at a concentration of at least about 0.05, 0.1, or 0.2 M based on the total volume of the liquid radiopharmaceutical pre-composition. Optionally, the buffer may be present at a concentration of up to about 0.5, 0.4, or 0.3 M based on the total volume of the liquid radiopharmaceutical pre-composition. Advantageously, the buffer may be present at a concentration of about 0.05 M to about 0.5 M, about 0.1 M to about 0.4 M, about 0.2 M to about 0.3 M, or about 0.25 M, based on the total volume of the liquid radiopharmaceutical pre-composition.

Optionally, the liquid radiopharmaceutical pre-composition may comprise: a. a precursor compound according to Formula II or a pharmaceutically acceptable salt thereof; b. a buffer, wherein the buffer provides the liquid radiopharmaceutical pre-composition with a pH of about 7.0 to about 8.9; c. a [$^{225}$Ac]Ac$^{3+}$ salt; and d. water.

Optionally, the liquid radiopharmaceutical pre-composition does not comprise a stabiliser. Optionally, the liquid radiopharmaceutical pre-composition does not comprise ascorbic acid or an ascorbate salt.

Optionally, the liquid radiopharmaceutical pre-composition does not comprise a specific activity between 1-10 GBq per mmol of DOTA-satoreotide.

Starter Composition

Aspects of the invention relate to a starter composition for the preparation of a liquid radiopharmaceutical pre-composition, comprising: a. a precursor compound according to Formula II or a pharmaceutically acceptable salt thereof; and b. a buffer, wherein the buffer is formulated to provide a pH of about 7.0 to about 8.9.

The liquid radiopharmaceutical pre-composition may optionally be as described or defined anywhere herein.

Advantageously, the precursor compound and the buffer may be in dried form. Optionally, the precursor compound and the buffer may be in lyophilised form. For example, where both the precursor compound and the buffer are in lyophilised form, the lyophilised form may be obtainable by lyophilising a solution comprising both the precursor compound and the buffer. Alternatively, the lyophilised form may be obtainable by combining a lyophilised precursor compound with a lyophilised buffer. Optionally, just the precursor compound may be in lyophilised form.

When the precursor compound and the buffer are in dried form, optionally lyophilised form, the buffer may be formulated to provide the pH of about 7.0 to about 8.9 on reconstitution of the precursor compound and buffer with sterile water for injection. Additionally, or alternatively, the buffer may be formulated to provide the pH of about 7.0 to about 8.9 on reconstitution of the precursor compound and buffer with water having a resistivity level of about 18.2 MΩ·cm. Such water is also known as Ultra Pure water, which is a term known in the art. Ultra Pure water can also be referred to as Type 1 water.

Conveniently, reconstitution can be conducted by reconstitution with any suitable amount of liquid. Optionally, reconstitution may be conducted by reconstitution with 1 mL of liquid. Sterile water for injection or Ultra Pure water can be used, suitably in an amount of 1 mL, as liquid in a test to determine the pH provided by the buffer. Sterile water for injection or Ultra Pure water, suitably in an amount of 1 mL, may also be used for preparation of the liquid radiopharmaceutical pre-composition, though it is to be understood the invention is not limited in this regard and other amounts or liquids may, optionally, be used for the preparation of the liquid radiopharmaceutical pre-composition.

Optionally, the starter composition may be a liquid composition and the buffer may be formulated to provide a pH of about 7.0 to about 8.9 in the starter composition. Optionally, the liquid composition does not comprise 0.25 M, based on the total volume of the liquid composition, Tris buffer at pH 8. Optionally, the liquid composition does not comprise 1 mg/mL, based on the total volume of the liquid composition, of the precursor compound. Optionally, the liquid composition does not comprise 0.25 M, based on the total volume of the liquid composition, Tris buffer at pH 8, and does not comprise 1 mg/mL, based on the total volume of the liquid composition, of the precursor compound.

Optionally, the buffer may provide a pH of at least about 7.1, 7.2, 7.3, 7.4, 7.5, 7.6, 7.7, 7.8 or 7.9. Suitably, the buffer may provide a pH of up to about 8.8, 8.7, 8.6, 8.5, 8.4, 8.3, 8.2 or 8.1. Advantageously, the buffer may provide a pH of about 7.1 to about 8.9, about 7.2 to about 8.8, about 7.3 to about 8.7, about 7.4 to about 8.6, about 7.5 to about 8.5, about 7.6 to about 8.4, about 7.7 to about 8.3, about 7.8 to about 8.2, or about 7.9 to about 8.1. For example, the buffer may provide a pH of about 8.0. Suitably, the buffer may be a pharmaceutically acceptable buffer. The skilled person is able to select a suitable buffer, using common techniques known in the art, that is suitable for maintaining such a pH. Optionally, the buffer may be selected from: Tris, HEPES, TES, MOPS, imidazole buffer, CAPS, ACES, TAPS, or a combination thereof. In some embodiments, the buffer is Tris buffer.

Optionally, the starter composition does not comprise a buffer formulated to provide a pH of 8.

Method of Preparing a Liquid Radiopharmaceutical Composition

Aspects of the invention relate to a method of preparing a liquid radiopharmaceutical composition, the method comprising: providing a liquid radiopharmaceutical pre-composition as described or defined anywhere herein; heating the liquid radiopharmaceutical pre-composition to generate a labelled composition; cooling the labelled composition; and diluting the labelled composition with a formulation solution; wherein the formulation solution comprises a formulation buffer that provides the liquid radiopharmaceutical composition with a pH of about 7.0 to about 8.9.

In principle, the heating of the liquid radiopharmaceutical pre-composition may be to any suitable temperature. Advantageously, the heating of the liquid radiopharmaceutical pre-composition may be at a temperature of at least about 75° C. Optionally, the heating of the liquid radiopharmaceutical pre-composition may be at a temperature of about 75° C. to about 85° C. The heating of the liquid radiopharmaceutical pre-composition may be for any suitable length of time. Advantageously, the heating of the liquid radiopharmaceutical pre-composition may be for at least about 20 minutes. Optionally, the heating of the liquid radiopharmaceutical pre-composition may be for about 20 minutes to about 30 minutes.

Suitably, the labelled composition may be diluted between 5 times and 100 times, between 10 times and 50 times, between 15 times and 30 times, or about 20 times by volume, with the formulation solution.

Conveniently, at least part of the cooling the labelled composition may occur by diluting the labelled composition with the formulation solution. Optionally, cooling the labelled composition occurs by diluting the labelled composition with the formulation solution. Suitably, cooling is to ambient temperature, optionally 25° C.

The liquid radiopharmaceutical composition may be as described or defined anywhere herein. Thus, it may comprise any of the features or limitations described. These features or limitations may be provided, where appropriate, via the formulation solution. For instance, the formulation solution may optionally bring the total volume of the liquid radiopharmaceutical composition up to about 1 mL to about 50 mL, about 5 mL to about 40 mL, about 10 mL to about 30 mL, about 15 mL to about 25 mL, about 18 mL to about 22 mL, or about 20 mL. Suitably, the formulation solution may comprise an aqueous diluent, as defined anywhere herein. Optionally, the formulation solution may comprise a pharmaceutically acceptable carrier and/or excipient, as defined anywhere herein. Optionally, the formulation solution may be formulated for parenteral application and may comprise parenteral diluents, as defined anywhere herein.

Optionally, the formulation solution may comprise a stabiliser. The stabiliser can optionally be selected from ascorbic acid, gentisic acid, glutathione, methionine, hydroquinone, polyoxyethylene (20) sorbitan monooleate, or structural analogues thereof, or pharmaceutically acceptable salts thereof, or combinations thereof. Optionally, the stabiliser may comprise ascorbic acid or a pharmaceutically acceptable salt thereof. Suitably, the pharmaceutically acceptable salt may be a sodium or potassium salt.

Suitably, the liquid radiopharmaceutical pre-composition may not comprise ascorbic acid, and the formulation solution may comprise ascorbic acid. In this way, ascorbic acid is not present during the radiolabelling step.

Optionally, the stabiliser, advantageously ascorbic acid or a pharmaceutically acceptable salt thereof, may be present at a concentration of greater than 350 mM, 373 mM, 400 mM, 425 mM, 450 mM, 500 mM, 550 mM or 600 mM based on the total volume of the formulation solution. Optionally, the stabiliser, advantageously ascorbic acid or a pharmaceutically acceptable salt thereof, may be present at a concentration of up to 2000 mM, 1500 mM, 1000 mM, 950 mM, 900 mM, 850 mM, or 800 mM based on the total volume of the formulation solution. Optionally, the stabiliser, advantageously ascorbic acid or a pharmaceutically acceptable salt thereof, may be present at a concentration of about 350 mM to about 2000 mM, about 375 mM to about 1500 mM, about 400 mM to about 1000 mM, about 425 mM to about 950 mM, about 450 mM to about 900 mM, about 500 mM to about 850 mM, about 550 mM to about 800 mM, or about 600 mM to about 750 mM based on the total volume of the formulation solution. In such embodiments, the labelled composition may advantageously be diluted at least 10 times with the formulation solution.

Optionally, the stabiliser, advantageously ascorbic acid or a pharmaceutically acceptable salt thereof, may be present at a concentration to provide a concentration of greater than 250 mM, 300 mM, 350 mM, 400 mM, 450 mM, 500 mM, 550 mM or 600 mM based on the total volume of the liquid radiopharmaceutical composition. Optionally, the stabiliser, advantageously ascorbic acid or a pharmaceutically acceptable salt thereof, may be present at a concentration to provide a concentration of up to 2000 mM, 1500 mM, 1000 mM, 950 mM, 900 mM, 850 mM, or 800 mM based on the total volume of the liquid radiopharmaceutical composition. Optionally, the stabiliser, advantageously ascorbic acid or a pharmaceutically acceptable salt thereof, may be present at a concentration to provide a concentration of about 250 mM to about 2000 mM, about 300 mM to about 1500 mM, about 350 mM to about 1000 mM, about 400 mM to about 950 mM, about 450 mM to about 900 mM, about 500 mM to about 850 mM, about 550 mM to about 800 mM, or about 600 mM to about 750 mM based on the total volume of the liquid radiopharmaceutical composition.

The formulation solution may optionally comprise a $^{225}$Ac chelator. Such a formulation solution can chelate any unbound $^{225}$Ac at least in part. Optionally, the chelator may comprise diethylenetriamine-N,N,N',N,N-pentaacetic acid (DTPA). Suitably, the liquid radiopharmaceutical composition may comprise the $^{225}$Ac chelator at a concentration from about 0.01 mg/mL to about 0.2 mg/mL, about 0.05 mg/mL to about 0.15 mg/mL, or about 0.07 mg/mL to about 0.12 mg/mL based on the total volume of the liquid radiopharmaceutical composition.

Conveniently, the liquid radiopharmaceutical composition may be separated into one or more unit dosage forms. Optionally, one or more unit dosage forms may be contained within a sealed container.

Kit

Aspects of the invention relate to a kit comprising: a precursor compound according to Formula II or a pharmaceutically acceptable salt thereof; and a buffer, wherein the buffer is formulated to provide a pH of about 7.0 to about 8.9.

Advantageously, the precursor compound and the buffer may be in dried form, optionally lyophilised form.

When the precursor compound and the buffer are in dried form, optionally lyophilised form, the buffer may be formulated to provide the pH of about 7.0 to about 8.9 on reconstitution of the precursor compound and buffer with sterile water for injection. Additionally, or alternatively, the buffer may be formulated to provide the pH of about 7.0 to about 8.9 on reconstitution of the precursor compound and buffer with water having a resistivity level of about 18.2 MΩ·cm. Such water is also known as Ultra Pure water, which is a term known in the art. Ultra Pure water can also be referred to as Type 1 water.

Conveniently, reconstitution can be conducted by reconstitution with any suitable amount of liquid. Optionally, reconstitution may be conducted by reconstitution with 1 mL of liquid. Sterile water for injection or Ultra Pure water can be used, suitably in an amount of 1 mL, as liquid in a test to determine the pH provided by the buffer. Sterile water for injection or Ultra Pure water, suitably in an amount of 1 mL, may also be used for preparation of the liquid radiopharmaceutical pre-composition, though it is to be understood the invention is not limited in this regard and other amounts or liquids may, optionally, be used for the preparation of a liquid radiopharmaceutical pre-composition from the kit.

Suitably, the precursor compound according to Formula II and the buffer may be mixed together. Alternatively, the precursor compound according to Formula II and the buffer may be provided separately.

Optionally, the kit can comprise a [$^{225}$Ac]Ac$^{3+}$ salt. Advantageously, the [$^{225}$Ac]Ac$^{3+}$ salt may be stored separately to the precursor compound. This helps to avoid radiolysis of the precursor compound. Usually, the [$^{225}$Ac]Ac$^{3+}$ salt would be provided separately to the kit.

Optionally, the kit may comprise instructions for preparing a liquid radiopharmaceutical composition with the kit, optionally as described or defined anywhere herein.

Optionally, the kit does not comprise a buffer formulated to provide a pH of 8.

Medical Use

Aspects of the invention relate to a liquid radiopharmaceutical composition as described or defined anywhere herein for use in treatment.

Aspects of the invention relate to use of a liquid radiopharmaceutical composition as described or defined anywhere herein in the manufacture of a medicament for use in treatment.

Aspects of the invention relate to use of a method of treatment of a patient in need thereof, the method comprising administering to a subject in need thereof a therapeutically effective amount of a liquid radiopharmaceutical composition as described or defined anywhere herein.

Optionally, the treatment in any of these aspects may be the treatment of cancer. Optionally, the treatment may be the treatment of tumors that express somatostatin receptor 2 (SSTR2). Optionally, the treatment may be the treatment of a neuroendocrine tumor (NET), small cell neuroendocrine carcinoma, small-cell lung carcinoma, large neuroendocrine carcinoma, typical carcinoid, or atypical carcinoid.

Optionally, the treatment may be of tumors that express SSTR2. In other words, the tumors are SSTR2-positive. Methods to identify an SSTR2 expressing tumor using an SSTR antagonist by in vivo imaging, for example, are known to the skilled person in the art.

Optionally the neuroendocrine tumor may be a neuroendocrine tumor of the gastrointestinal tract.

Optionally, the cancer may be an SSTR2-positive subset of breast, prostate, pancreatic, neuroendocrine, Merkel-cell carcinomas and hepatocellular carcinomas.

Optionally, the treatment may be of humans and/or non-human mammalian animals, preferably humans.

Suitably, the liquid radiopharmaceutical composition may be for administration, or may be administered to a subject in need thereof, at a dose of between 2 MBq and 10 MBq. Optionally, the dose may be 2.4 to 9.6 MBq+/−10%. Optionally, the liquid radiopharmaceutical composition may be for administration, or may be administered to a subject in need thereof, every 2 to 8 weeks. Optionally, the liquid radiopharmaceutical composition may be for administration, or may be administered to a subject in need thereof, at a dose of between 2 MBq and 10 MBq every 2 to 8 weeks.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Suitably, the therapeutically effective amount may be that which may treat or alleviate the disease or symptoms of the disease at a reasonable benefit/risk ratio applicable to any medical treatment. However, it is to be understood that the total daily usage of the compounds and compositions described herein may be decided by an attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

BRIEF DESCRIPTION OF THE DRAWINGS

One or more embodiments of the invention will now be described, by way of example only, with reference to the accompanying drawings, in which:

FIG. 1 shows the radiochemical purity of a [$^{225}$Ac]Ac-DOTA-satoreotide radiopharmaceutical composition in accordance with an embodiment of the invention at t=0 h, t=24 h, t=96 h, and t=168 h from EoP, as determined by radio-TLC.

Example 1

The preparation of [$^{225}$Ac]Ac-DOTA-Satoreotide was achieved by reacting DOTA-satoreotide (100-500 μg from a 1.0 mg/mL sol.) with $^{225}$Ac[AcCl$_3$](2.0-10.0 MBq) from 10 μCi/μL (0.37 MBq/μL) HCl (0.04 M, aqueous) solution.

The DOTA-Satoreotide was diluted with up to 1 mL TRIS HCl buffer (0.25 M, pH 8.0) and $^{225}$Ac[AcCl$_3$] was added.

The reaction mixture of a total volume of up to 1 mL was heated at 80° C. for 20-30 min.

Upon reaction completion, the mixture was directly cooled down with formulation solution (123.7 mg/mL sodium ascorbate buffer) to yield a 20 mL [$^{225}$Ac]Ac-DOTA-satoreotide stock solution. Reaction completion is referred to as the "end-of-production" (EoP) time, or t=0 h as used in the following results.

The radiopharmaceutical composition incorporated the $^{225}$Ac as [$^{225}$Ac]Ac-DOTA-satoreotide at 99.5% at End-of-Preparation (see FIG. 1). This was determined by radio thin-layer chromatography (TLC) as set out below.

The radiopharmaceutical composition was found to remain stable such that a purity of 95.8% was obtained after 168 hours at ambient temperatures (see FIG. 1). This was determined by radio TLC as set out below.

Radio TLC Method

Radio-TLC was performed at T=0 h and at various time points subsequent to the radiolabeling procedure. To run the procedure, 5 μL of reaction solution was spotted on a TLC plate (RP-C18 silica glass plates) at about 1.5 cm from bottom edge. The TLC plate was developed using a mobile phase mixture of ammonium acetate 25% and methanol (40:60 Vol.-%) with an elution length of about 5-6 cm. The TLC plate was dried and measured on a phosphor imager (Perkin Elmer Cyclone Plus Storage Phosphor system) once secular equilibrium of $^{225}$Ac and $^{221}$Fr/$^{213}$Bi was reached (>6 hours after development). Free Ac(III) stays at the origin while $^{225}$Ac-DOTA-Satoreotide travels with the eluent front.

In FIG. 1, "T=Xh, read Yh" means that a sample was taken and developed at T=Xh but analyzed Yh after development of the TLC plate, to account for equilibrium of the daughters.

DISCUSSION

By comparison, where Handula et al conducted the complexation reaction at acidic pH and achieved a radiochemical yield of up to 95.1%, Example 1 achieves an enhanced radiochemical yield of 99.5%.

In addition, the inventors have been able to achieve, stabilities of 98.9% radiochemical purity at 96 h from EoP and 95.8% radiochemical purity at 168 h from EoP.

This application expressly encompasses each and every clause set forth below:

(1) A liquid radiopharmaceutical composition comprising:
 a. a radiopharmaceutical compound according to Formula I

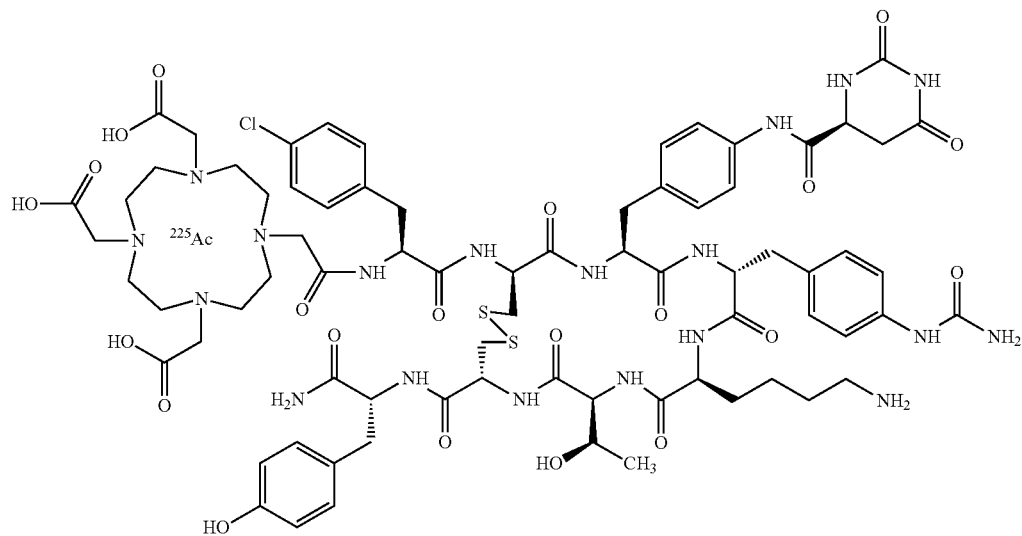

Formula I or a pharmaceutically acceptable salt thereof; and
b. a buffer, and the buffer provides the radiopharmaceutical composition with a pH of about 7.0 to about 8.9.

(2) A liquid radiopharmaceutical composition according to clause (1), and the radiopharmaceutical compound is present at a concentration equivalent to about 0.1 MBq/mL to about 0.5 MBq/mL based on the total volume of the liquid radiopharmaceutical composition.

(3) A liquid radiopharmaceutical composition according to clause (1) or (2), and the buffer is present at a concentration of between about 1 mM to about 100 mM based on the total volume of the liquid radiopharmaceutical composition.

(4) A liquid radiopharmaceutical composition according to any preceding clause, further comprises a stabiliser, optionally selected from ascorbic acid, gentisic acid, glutathione, methionine, hydroquinone, polyoxyethylene (20) sorbitan monooleate, or structural analogues thereof, or pharmaceutically acceptable salts thereof, or combinations thereof.

(5) A liquid radiopharmaceutical composition according to clause (4), and the stabiliser is ascorbic acid or a pharmaceutically acceptable ascorbate salt.

(6) A liquid radiopharmaceutical composition according to clause (4) or clause (5), and the stabiliser is present at a concentration of greater than 350 mM based on the total volume of the liquid radiopharmaceutical composition.

(7) A liquid radiopharmaceutical composition according to any preceding clause, and the composition retains a radiochemical purity of >91% after 168 hours at ambient temperature.

(8) A liquid radiopharmaceutical pre-composition comprising:
a. a precursor compound according to Formula II

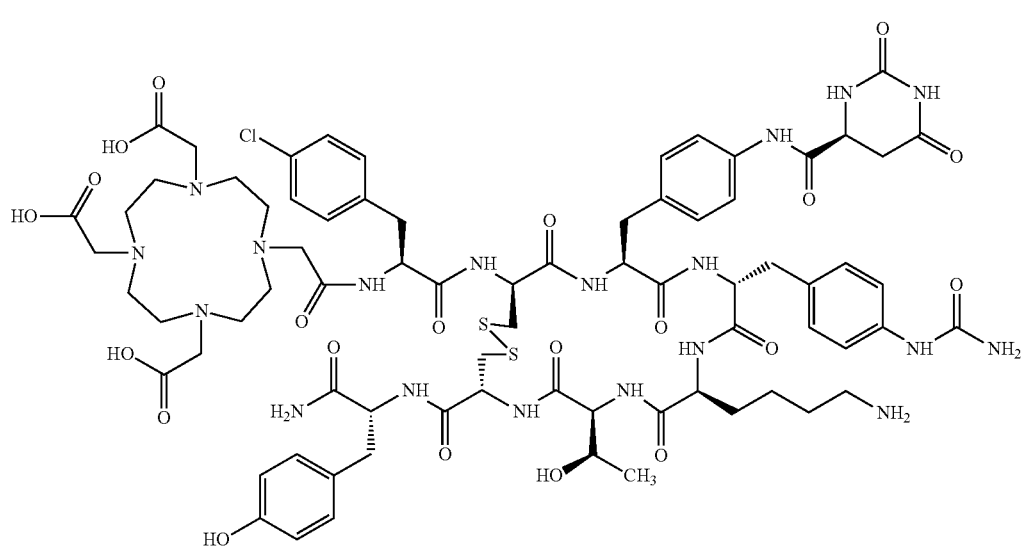

Formula II or a pharmaceutically acceptable salt thereof;
b. a buffer, and the buffer provides the liquid radiopharmaceutical pre-composition with a pH of about 7.0 to about 8.9; and
c. a [$^{225}$Ac]Ac$^{3+}$ salt.

(9) A liquid radiopharmaceutical pre-composition according to clause (8), and the [$^{225}$Ac]Ac$^{3+}$ salt is present at a concentration equivalent to about 0.1 MBq/mL to about 20 MBq/mL based on the total volume of the liquid radiopharmaceutical pre-composition.

(10) A liquid radiopharmaceutical pre-composition according to clause (8) or clause (9) and the precursor compound is present at a concentration of about 0.01 mg/mL to about 10 mg/mL based on the total volume of the liquid radiopharmaceutical pre-composition.

(11) A liquid radiopharmaceutical pre-composition according to any one of clauses (8) to (10), and the buffer is present at a concentration of about 0.01 M to about 1 M based on the total volume of the liquid radiopharmaceutical pre-composition.

(12) A starter composition for the preparation of a liquid radiopharmaceutical pre-composition, optionally according to any one of clauses (8) to (11), comprising:
a. a precursor compound according to Formula II

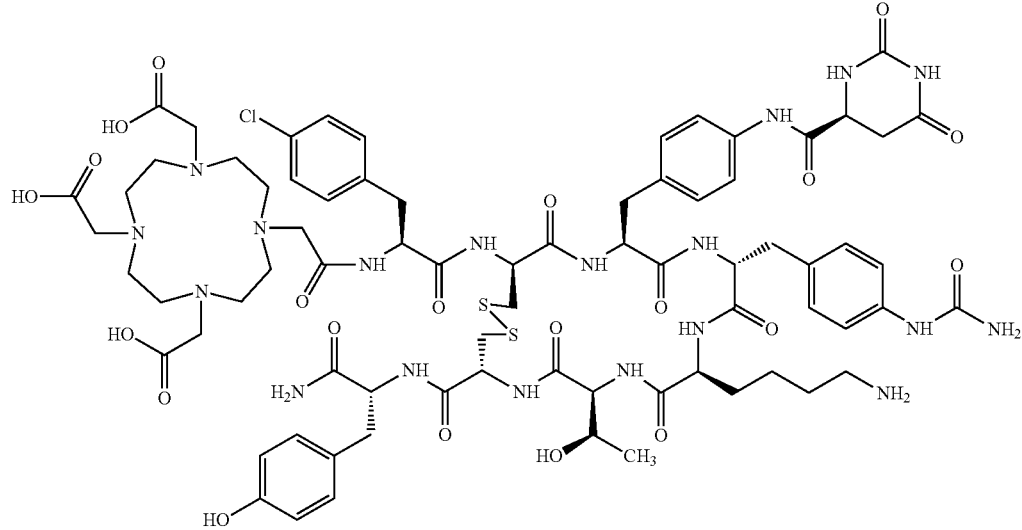

Formula II or a pharmaceutically acceptable salt thereof; and
b. a buffer, and the buffer is formulated to provide a pH of about 7.0 to about 8.9.

(13) A starter composition according to clauses (12), and the precursor compound and the buffer are in dried form, optionally lyophilised form.

(14) A starter composition according to clause (13), and the buffer is formulated to provide the pH of about 7.0 to about 8.9 on reconstitution of the precursor compound and buffer with distilled water.

(15) A starter composition according to clause (12), and the starter composition is a liquid composition and the buffer is formulated to provide a pH of about 7.0 to about 8.9 in the starter composition.

(16) A method of preparing a liquid radiopharmaceutical composition, the method comprising:
i. providing a liquid radiopharmaceutical pre-composition according to any one of clauses (8) to (11);
ii. heating the liquid radiopharmaceutical pre-composition to generate a labelled composition;
iii. cooling the labelled composition; and
iv. diluting the labelled composition with a formulation solution; and the formulation solution comprises a formulation buffer that provides the liquid radiopharmaceutical composition with a pH of about 7.0 to about 8.9.

(17) A method according to clause (16), and the heating of the liquid radiopharmaceutical pre-composition is at a temperature of at least about 75° C.

(18) A method according to clause (16) or clause (17), and the heating of the liquid radiopharmaceutical pre-composition is for at least about 20 minutes.

(19) A method according to any one of clauses (16) to (18), and the labelled composition is diluted between 5 times and 100 times with the formulation solution.

(20) A method according to any one of clauses (16) to (19), and at least part of cooling the labelled composition occurs on diluting the labelled composition with the formulation solution.

(21) A method according to any one of clauses (16) to (20), and the liquid radiopharmaceutical composition is as defined in any of clauses (1) to (7).

(22) A kit comprising:
a. a precursor compound according to Formula II

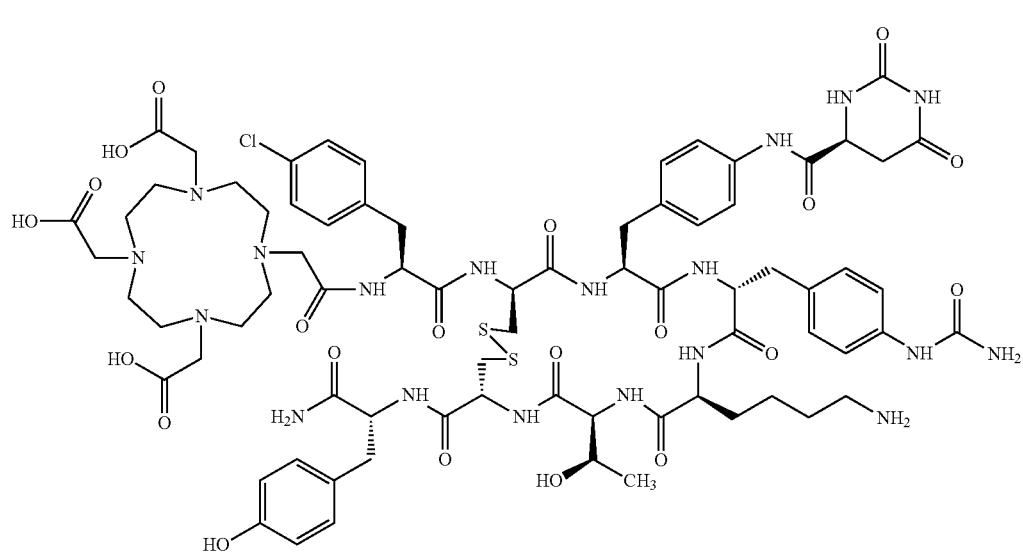

Formula II or a pharmaceutically acceptable salt thereof; and
b. a buffer, and the buffer is formulated to provide a pH of about 7.0 to about 8.9.

(23) A kit according to clause (22), and the precursor compound and the buffer are in dried form, optionally lyophilised form.

(24) A kit according to clause (22) or clause (23), and the buffer is formulated to provide the pH of about 7.0 to about 8.9 on reconstitution of the precursor compound and buffer with distilled water.

(25) A kit according to any one of clauses (22) to (24), and the precursor compound according to Formula II and the buffer are mixed together.

(26) A kit according to any one of clauses (22) to (24), and the precursor compound according to Formula II and the buffer are provided separately.

(27) A kit according to any one of clauses (22) to (26), further comprising: c. a $[^{225}Ac]Ac^{3+}$ salt.

(28) A kit according to any one of clauses (22) to (27), further comprising instructions for preparing a liquid radiopharmaceutical composition with the kit.

(29) A kit according to clause (28), and the instructions further comprise a method according to any one of clauses (16) to (21).

(30) A liquid radiopharmaceutical composition according to any one of clauses (1) to (7) for use in treatment.

(31) Use of a liquid radiopharmaceutical composition according to any one of clauses (1) to (7) in the manufacture of a medicament for use in treatment.

(32) A method of treatment of a patient in need thereof, and the method comprises administering to a subject in need thereof a therapeutically effective amount of a liquid radiopharmaceutical composition according to any one of clauses (1) to (7).

(33) A liquid radiopharmaceutical composition for use according to clause (30), a use in the manufacture of a medicament according to clause (31), or a method of treatment according to clause (32), and the treatment is the treatment of cancer.

(34) A liquid radiopharmaceutical composition for use, a use in the manufacture of a medicament, or a method of treatment, according to clause (33), and the treatment of cancer is the treatment of tumors that express somatostatin receptor 2 (SSTR2).

(35) A liquid radiopharmaceutical composition for use, a use in the manufacture of a medicament, or a method of treatment, according to clause (33) or (34), and the treatment of cancer is the treatment of a neuroendocrine tumor (NET), small cell neuroendocrine carcinoma, large neuroendocrine carcinoma, typical carcinoid, or atypical carcinoid.

---

SEQUENCE LISTING

```
Sequence total quantity: 1
SEQ ID NO: 1           moltype = AA  length = 8
FEATURE                Location/Qualifiers
source                 1..8
                       mol_type = protein
                       organism = synthetic construct
SITE                   1
                       note = para-chlorophenylalanine
SITE                   2
                       note = D-cysteine
SITE                   3
                       note =
```

```
                    [(2,6-dioxo-hexahydro-pyrimidine-4-carbonyl)-amino]-phenyla
                    lanine
SITE            4
                    note = 4-amino-phenylcarbamoyl (4-ureido-phenylalanine)
SITE            8
                    note = D-tyrosine
DISULFID        2..7
                    note = disulfide bridge
SEQUENCE: 1
XCXXKTCY                                                                     8
```

The invention claimed is:

1. A method of preparing a liquid radiopharmaceutical composition comprising a radiopharmaceutical compound according to Formula I

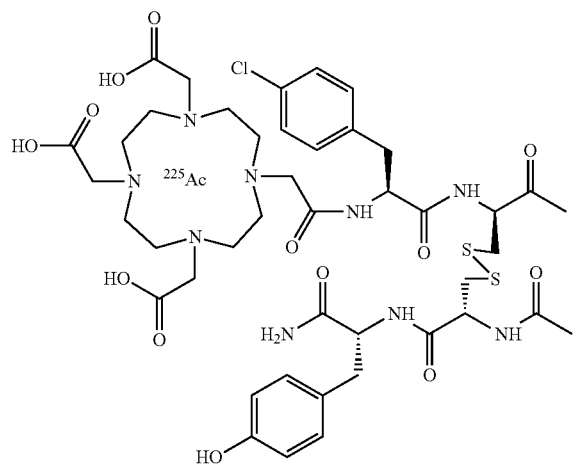

Formula I

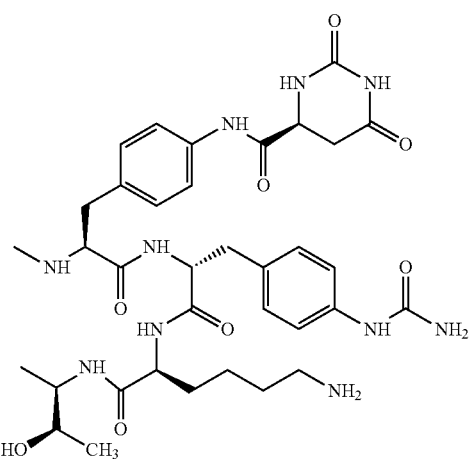

or a pharmaceutically acceptable salt thereof, the method comprising:
  providing a liquid radiopharmaceutical pre-composition comprising:
    i. a precursor compound according to Formula II

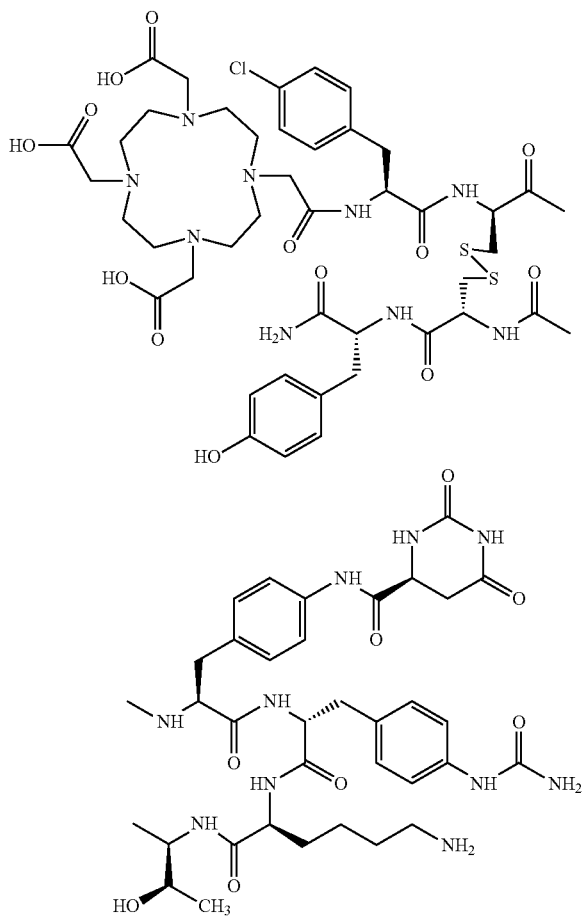

Formula II or a pharmaceutically acceptable salt thereof;
    ii. a buffer, wherein the buffer provides the liquid radiopharmaceutical pre-composition with a pH of about 8.0 to about 8.9; and
    iii. a [$^{225}$Ac]Ac$^{3+}$ salt;
  heating the liquid radiopharmaceutical pre-composition to generate a labelled composition;
  cooling the labelled composition; and
  diluting the labelled composition with a formulation solution; wherein the formulation solution comprises a formulation buffer that provides the liquid radiopharmaceutical composition with a pH of about 8.0 to about 8.9.

2. A method according to claim 1, wherein the heating of the liquid radiopharmaceutical pre-composition is for at least about 75° C.

3. A method according to claim 1, wherein the heating of the liquid radiopharmaceutical pre-composition is for at least about 20 minutes.

4. A method according to claim 1, wherein the labelled composition is diluted between 5 times and 100 times with the formulation solution.

5. A method according to claim 1, wherein at least part of cooling the labelled composition occurs on diluting the labelled composition with the formulation solution.

6. A method according to claim 1, wherein the radiopharmaceutical compound is present at a concentration equivalent to about 0.1 MBq/mL to about 0.5 MBq/mL based on the total volume of the liquid radiopharmaceutical composition.

7. A method according to claim 1, wherein the buffer and formulation buffer are present at a combined concentration of between about 1 mM to about 100 mM based on the total volume of the liquid radiopharmaceutical composition.

8. A method according to claim 1, wherein the liquid radiopharmaceutical composition comprises a stabiliser selected from ascorbic acid, gentisic acid, glutathione, methionine, hydroquinone, polyoxyethylene (20) sorbitan monooleate, or structural analogues thereof, or pharmaceutically acceptable salts thereof, or combinations thereof.

9. A method according to claim 8, wherein the stabiliser is ascorbic acid or a pharmaceutically acceptable ascorbate.

10. A method according to claim 8, wherein the stabiliser is present at a concentration of greater than 350 mM based on the total volume of the liquid radiopharmaceutical composition.

11. A method according to claim 1, wherein the liquid radiopharmaceutical composition retains a radiochemical purity of >91% after 168 hours at ambient temperature.

* * * * *